United States Patent [19]
Weissleder et al.

[11] Patent Number: 6,083,486
[45] Date of Patent: Jul. 4, 2000

[54] INTRAMOLECULARLY-QUENCHED NEAR INFRARED FLUORESCENT PROBES

[75] Inventors: Ralph Weissleder, Charlestown; Ching-Hsuan Tung, Natick; Umar Mahmood, Boston; Lee Josephson; Alexei Bogdanov, both of Arlington, all of Mass.

[73] Assignee: The General Hospital Corporation, Boston, Mass.

[21] Appl. No.: 09/079,447

[22] Filed: May 14, 1998

[51] Int. Cl.[7] .......................... A61K 49/00; G01N 31/00; G01N 33/48
[52] U.S. Cl. ................................ 424/9.6; 424/9.1; 424/9; 424/1.11; 424/1.65; 600/9
[58] Field of Search .................................. 424/1.11, 1.65, 424/9.1, 9.6, 9.7, 9.8, 1.37, 1.69; 530/300, 331, 328, 329; 600/9

[56] References Cited

U.S. PATENT DOCUMENTS

| | | | |
|---|---|---|---|
| 5,403,928 | 4/1995 | Arrhenuis | 540/128 |
| 5,593,658 | 1/1997 | Bogdanov et al. | 424/9.34 |
| 5,641,878 | 6/1997 | Dandliker et al. | 540/128 |
| 5,661,035 | 8/1997 | Tsien et al. | 436/63 |
| 5,677,199 | 10/1997 | Arrhenuis | 436/536 |
| 5,846,703 | 12/1998 | Devlin et al. | 435/5 |
| 5,876,946 | 3/1999 | Burbaum et al. | 435/7.1 |

OTHER PUBLICATIONS

Ballou et al., "Tumor Labeling In Vivo Using Cyanine–conjugated Monoclonal Antibodies", Cancer Immunol. Immunother 41:257–263, 1995.

Bogdanov et al., "Long–circulating Blood Pool Imaging Agents", Advanced Drug Delivery Reviews 16:335–348, 1995.

Denmeade et al., "Specific and Efficient Peptide Substrates for Assaying the Proteolytic Activity of Prostate–specific Antigen", Cancer Research 57:4924–4930, 1997.

Folli et al., "Antibody–Indocyanin Conjugates for Immunophotodetection of Human Squamous Cell Carcinoma In Nude Mice", Cancer Res. 54:2643–2649, 1994.

Gulnik et al., "Design of Sensitive Fluorogenic Substrates for Human Cathepsin D", FEBS Letters 413:379–384 1997.

Neri et al., "Targeting by Affinity–matured Recombinant Antibody Fragments of an Angiogenesis Associated Fibronectin Isoform", Nature Biotechnology 15:1271–1275, 1997.

Tromberg et al., "Non–invasive Measurements of Breast Tissue Optical Properties Using Frequency–domain Photo Migration", Phil. Trans. R. Soc. London B 352:661–667, 1997.

Wyatt, "Cerebral Oxygenation and Haemodynamics in the Fetus and Newborn Infant", Phil. Trans. R. Soc. London B 352:701–706, 1997.

*Primary Examiner*—S. Mark Clardy
*Assistant Examiner*—Dameron Jones
*Attorney, Agent, or Firm*—Fish & Richardson P.C.

[57] ABSTRACT

An intramolecularly-quenched, near infrared fluorescence probe that emits substantial fluorescence only after interaction with a target tissue (i.e., activation) is disclosed. The probe includes a polymeric backbone and a plurality of near infrared fluorochromes covalently linked to the backbone at fluorescence-quenching interaction-permissive positions separable by enzymatic cleavage at fluorescence activation sites. The probe optionally includes protective chains or fluorochrome spacers, or both. Also disclosed are methods of using the intramolecularly-quenched, near infrared fluorescence probes for in vivo optical imaging.

19 Claims, 7 Drawing Sheets

1. Cy5.5
Ex=675
Em=694
ε=250,000
Q=28%

2. Cy5
Ex=649
Em=670
ε=250,000
Q=28%

3. IRD41
Ex=787
Em=807
ε=200,000
Q=16.5%

4. IRD700
Ex=685
Em=705
ε=170,000
Q=50%

5. NIR-1
Ex=663
Em=685
ε=75,000

6. LaJolla Blue
Ex=680
Em=700
ε=170,000
Q=70%

INTRAMOLECULARLY-QUENCHED NEAR INFRARED FLUORESCENT PROBES

FIELD OF THE INVENTION

The invention relates to biochemistry, cell biology, and in vivo optical imaging.

BACKGROUND OF THE INVENTION

Optically based biomedical imaging techniques have advanced over the past decade due to factors including developments in laser technology, sophisticated reconstruction algorithms and imaging software originally developed for non-optical, tomographic imaging modes such as CT and MRI. Visible wavelengths are used for optical imaging of surface structures by means of endoscopy and microscopy.

Near infrared wavelengths (approx. 700–1000 nm) have been used in optical imaging of internal tissues, because near infrared radiation exhibits tissue penetration of up to 6–8 centimeters. See, e.g., Wyatt, 1997, "Cerebral oxygenation and haemodynamics in the fetus and newborn infant," *Phil. Trans. R. Soc. London B* 352:701–706; Tromberg et al., 1997, "Non-invasive measurements of breast tissue optical properties using frequency-domain photo migration," *Phil. Trans. R. Soc. London B* 352:661–667.

Advantages of near infrared imaging over other currently used clinical imaging techniques include: the potential for simultaneous use of multiple, distinguishable probes (important in molecular imaging); high temporal resolution (important in functional imaging); high spatial resolution (important in in vivo microscopy); and safety (no ionizing radiation).

In near infrared fluorescence imaging, filtered light or a laser with a defined bandwidth is used as a source of excitation light. The excitation light travels through body tissues. When it encounters a near infrared fluorescent molecule ("contrast agent"), the excitation light is absorbed. The fluorescent molecule then emits light (fluorescence) spectrally distinguishable (slightly longer wavelength) from the excitation light. Despite good penetration of biological tissues by near infrared light, conventional near infrared fluorescence probes are subject to many of the same limitations encountered with other contrast agents, including low target/background ratios.

SUMMARY OF THE INVENTION

We have developed intramolecularly-quenched, near infrared fluorescence probes that emit substantial fluorescence only after interaction with a target tissue, i.e., "activation." This increases the target/background ratio by several orders of magnitude and enables non-invasive, near infrared imaging of internal target tissues in vivo, based on enzymatic activity present in the target tissue.

Accordingly, the invention features an intramolecularly-quenched fluorescence probe comprising a polymeric backbone and a plurality of near infrared fluorochromes covalently linked to the backbone at fluorescence-quenching interaction-permissive positions separable by enzymatic cleavage at fluorescence activation sites.

The backbone can be any biocompatible polymer. For example, it can be a polypeptide, a polysaccharide, a nucleic acid, or a synthetic polymer. Polypeptides useful as a backbone include, for example, polylysine, albumins, and antibodies. Poly(L-lysine) is a preferred polypeptide backbone. The backbone also can be a synthetic polymer such as polyglycolic acid, polylactic acid, poly(glycolic-colactic) acid, polydioxanone, polyvalerolactone, poly-$\epsilon$-caprolactone, poly(3-hydroxybutyrate, poly(3-hydroxyvalerate) polytartronic acid, and poly($\beta$-malonic acid).

The probe can include one or more protective chains covalently linked to the backbone. Suitable protective chains include polyethylene glycol, methoxypolyethylene glycol, methoxypolypropylene glycol, copolymers of polyethylene glycol and methoxypolypropylene glycol, dextran, and polylactic-polyglycolic acid. In some embodiments of the invention, the backbone is polylysine and the protective chains are methoxypolyethylene glycol.

Fluorescence activation sites can be located in the backbone, e.g., when the fluorochromes linked directly to $\epsilon$-amino groups of polylysine. Alternatively, each fluorochrome can be linked to the backbone by a spacer containing a fluorescence activation site. The spacers can be oligopeptides. Oligopeptide sequences useful as spacers include: Arg-Arg; Arg-Arg-Gly; Gly-Pro-Ile-Cys-Phe-Phe-Arg-Leu-Gly (SEQ ID NO:1); and His-Ser-Ser-Lys-Leu-Gln-Gly (SEQ ID NO:2).

Examples of fluorochromes useful in this invention include Cy5.5, Cy5, IRD41, IRD700, NIR-1, and LaJolla Blue. The fluorochromes can be covalently linked to the backbone, or spacers, using any suitable reactive group on the fluorochrome and a compatible functional group on the backbone or spacer. A probe according to this invention also can include a targeting moiety such as an antibody, antigen-binding antibody fragment, a receptor-binding polypeptide, or a receptor-binding polysaccharide.

The invention also features an in vivo optical imaging method. The method includes: (a) administering to a living animal or human an intramolecularly-quenched fluorescence probe that accumulates preferentially in a target tissue, and comprises a fluorochrome attachment moiety and a plurality of near infrared fluorochromes covalently linked to the fluorochrome attachment moiety at fluorescence-quenching interaction-permissive positions separable by enzymatic cleavage at fluorescence activation sites; (b) allowing time for (1) the probe to accumulate preferentially in the target tissue, and (2) enzymes in the target tissue to activate the probe by enzymatic cleavage at fluorescence activation sites, if the target tissue is present; (c) illuminating the target tissue with near infrared light of a wavelength absorbable by the fluorochromes; and (d) detecting fluorescence emitted by the fluorochromes. Preferably, the fluorochrome attachment moiety is a polymeric backbone. Alternatively, it can be a monomeric, dimeric, or oligomeric molecule.

The invention also features an in vivo optical imaging method comprising: (a) administering to a living animal or human an intramolecularly-quenched fluorescence probe comprising a fluorochrome attachment moiety and a plurality of near infrared fluorochromes covalently linked to the fluorochrome attachment moiety at fluorescence-quenching interaction-permissive positions separable by enzymatic cleavage at fluorescence activation sites, which enzymatic cleavage occurs preferentially in a target tissue; (b) allowing time for enzymes in the target tissue to activate the probe by enzymatic cleavage at fluorescence activation sites, if the target tissue is present; (c) illuminating the target tissue with near infrared light of a wavelength absorbable by the fluorochromes; and (d) detecting fluorescence emitted by the fluorochromes. Preferably, the fluorochrome attachment moiety is a polymeric backbone. Alternatively, it can be a monomeric, dimeric, or oligomeric molecule.

As used herein, "backbone" means a biocompatible polymer to which near infrared fluorochromes are covalently linked in fluorescence-quenching interaction-permissive positions.

As used herein, "fluorescence activation site" means a covalent bond within a probe, which bond is: (1) cleavable by an enzyme present in a target tissue, and (2) located so that its cleavage liberates a fluorochrome from being held in a fluorescence-quenching interaction-permissive position.

As used herein, "fluorescence-quenching interaction-permissive positions" means the positions of two or more atoms (in a single polymer) to which fluorochromes can be covalently linked (directly or indirectly through a spacer) so that the fluorochromes are maintained in a position relative to each other that permits them to interact photochemically and quench each other's fluorescence.

As used herein, "fluorochrome attachment moiety" means a molecule to which two or more fluorochromes are covalently linked (directly or through a spacer) and maintained in fluorescence-quenching interaction-permissive positions relative to one another.

As used herein, "protective chain" means a biocompatible polymeric moiety covalently linked to the backbone of a probe to inhibit undesired biodegradation, clearance, or immunogenicity of the backbone.

As used herein, "targeting moiety" means a moiety bound covalently or noncovalently to a self-quenched probe, which moiety enhances the concentration of the probe in a target tissue relative to surrounding tissue.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Although methods and materials similar or equivalent to those described herein can be used in the practice or testing of the present invention, the preferred methods and materials are described below. The materials, methods, and examples are illustrative only and not intended to be limiting. Other features and advantages of the invention will be apparent from the detailed description, and from the claims.

BRIEF DESCRIPTION OF THE DRAWINGS

FIG. 2A includes the structures of Cy5.5, Cy5, IRD41, and IRD700. FIG. 2B includes the structures of NIR-1 and LaJolla Blue.

DETAILED DESCRIPTION

Probe Design and Synthesis

Figure 1A:
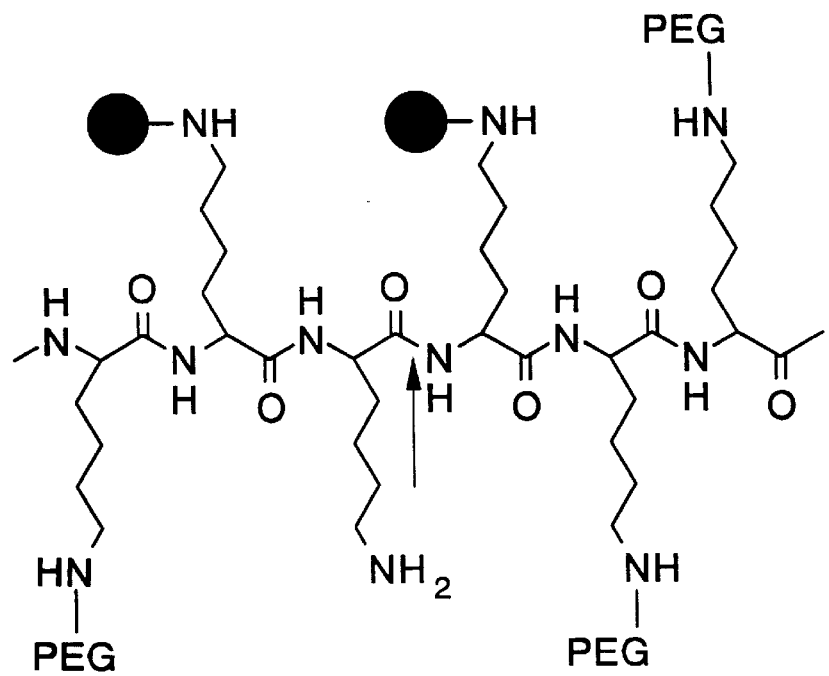
FIGS. 1A and 1B are schematic diagrams indicating the chemical components, and their structural arrangement, in probes representing two embodiments of the invention.
Figure 1B:
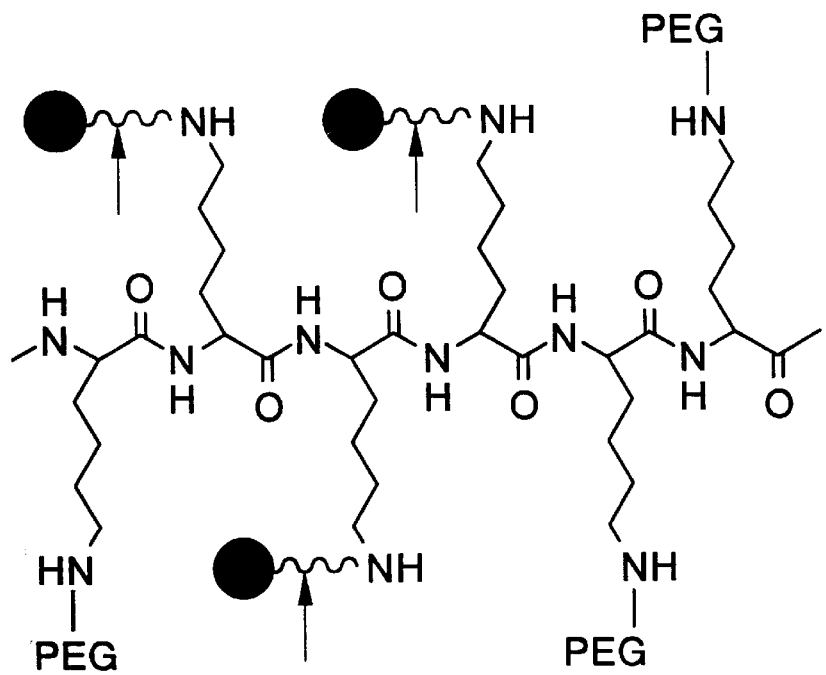

Probe backbone design will depend on considerations such as biocompatibility (e.g., toxicity and immunogenicity), serum half-life, useful functional groups (for conjugating fluorochromes, spacers, and protective groups), and cost. Useful types of backbone include polypeptides (polyamino acids), polyethyleneamines, polysaccharides, aminated polysaccharides, aminated oligosaccharides, polyamidoamines, polyacrylic acids and polyalcohols. A preferred backbone consists of a polypeptide formed from L-amino acids. When polylysine is used as a backbone, the $\epsilon$-amino groups on the side chains of the polylysine can serve as convenient reactive groups for covalent linkage of fluorochromes and spacers (FIGS. 1A and 1B). When the backbone is a polypeptide, preferably the molecular weight of the probe is from 2 kD to 1000 kD. More preferably, its molecular weight is from 4 kd to 500 kd.

A backbone may be chosen or designed so as to have a suitably long in vivo persistence (half-life) inherently. Therefore, protective chains are not necessary in some embodiments of the invention. Alternatively, a rapidly-biodegradable backbone such as polylysine can be used in combination with covalently-linked protective chains. Examples of useful protective chains include polyethylene glycol (PEG), methoxypolyethylene glycol (MPEG), methoxypolypropylene glycol, polyethylene glycol-diacid, polyethylene glycol monoamine, MPEG monoamine, MPEG hydrazide, and MPEG imidazole. The protective chain can also be a block-copolymer of PEG and a different polymer such as a polypeptide, polysaccharide, polyamidoamine, polyethyleneamine or polynucleotide. Synthetic, biocompatible polymers are discussed generally in Holland et al., 1992, "Biodegradable Polymers," *Advances in Pharmaceutical Sciences* 6:101–164.

A useful backbone-protective chain combination is methoxypoly(ethylene)glycol-succinyl-N-$\epsilon$-poly-L-lysyine (PL-MPEG). The synthesis of this material, and other polylysine backbones with protective chains, is described in Bogdanov et al., U.S. Pat. No. 5,593,658 and Bogdanov et al., 1995, *Advanced Drug Delivery Reviews* 16:335–348.

Figure 2A:
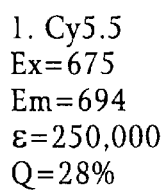
FIGS. 2A and 2B are the chemical structures of six near infrared fluorochromes.
Figure 2A:
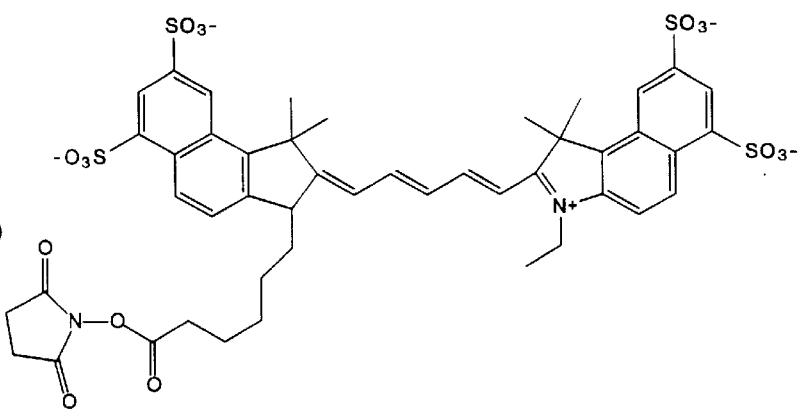
Figure 2A:
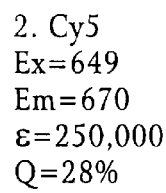
Figure 2A:
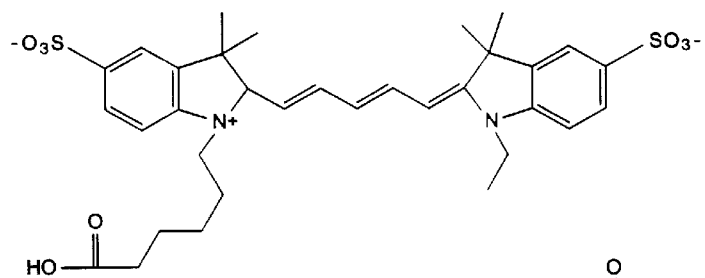
Figure 2A:
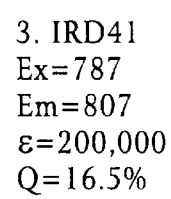
Figure 2A:
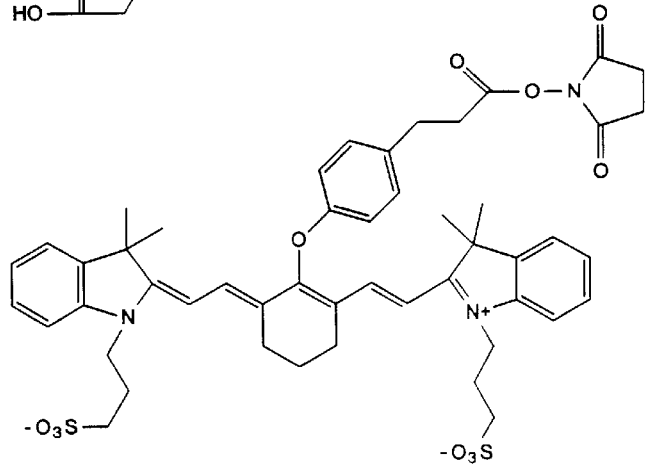
Figure 2A:
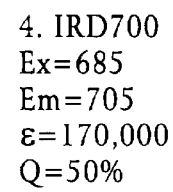
Figure 2A:
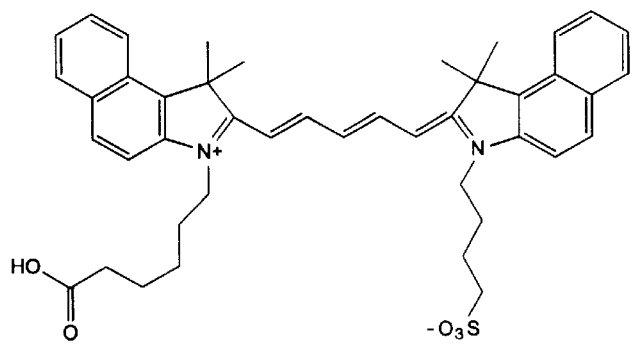
Figure 2B:
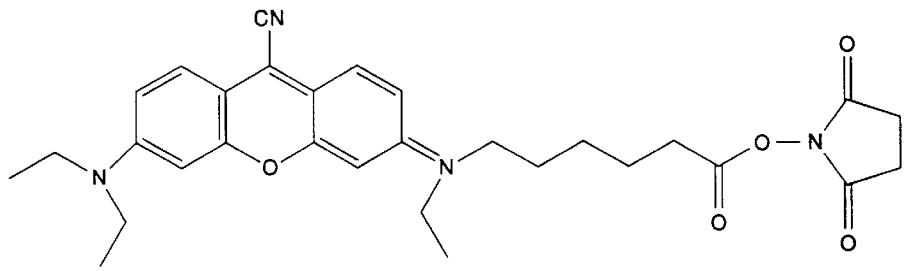
Figure 2B:
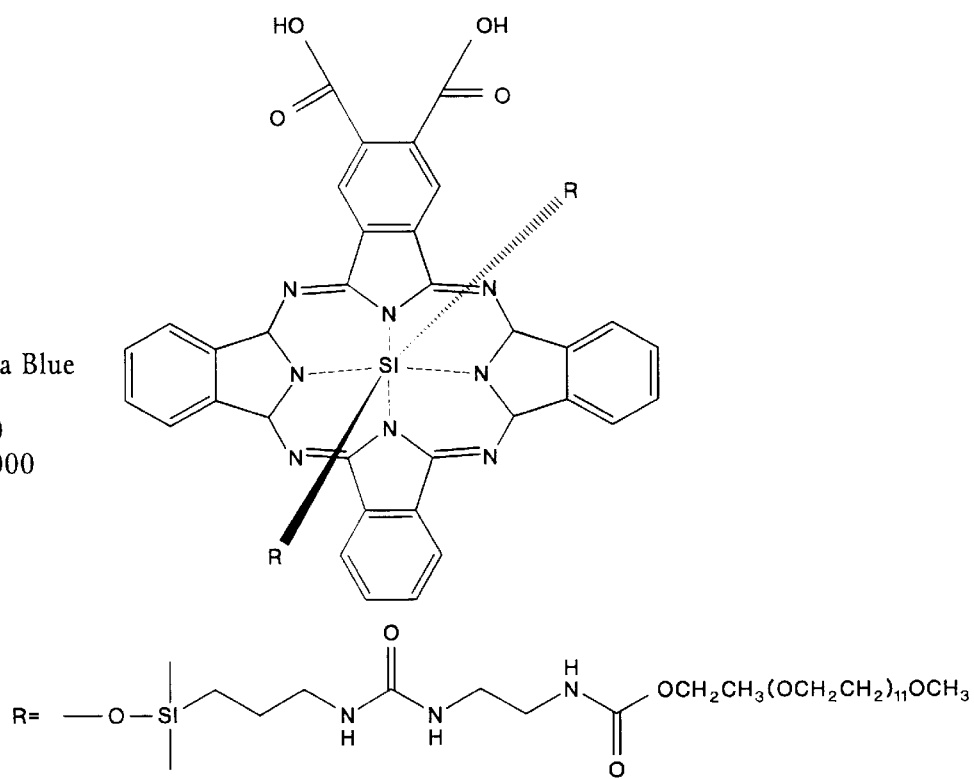

Various near infrared fluorochromes are commercially available (Cy5.5 and Cy5; Amersham, Arlington Hts., Ill.; IRD41 and IRD700, LI-COR, Lincoln, Neb.; NIR-1, Dejindo, Kumamoto, Japan; LaJolla Blue, Diatron, Miami, Fla.) and can be used to construct probes according to this invention. Fluorescent probes with excitation and emission wavelengths in the near infrared spectrum are used, i.e., 650–1300 nm. Use of this portion of the electromagnetic spectrum maximizes tissue penetration and minimizes absorption by physiologically abundant absorbers such as hemoglobin (<650 nm) and water (>1200 nm). Ideal near infrared fluorochromes for in vivo use exhibit: (1) narrow spectral characteristics, (2) high sensitivity (quantum yield), (3) biocompatibility, and (4) decoupled absorption and excitation spectra. Table 1 summarizes information on the properties of six commercially-available near infrared fluorochromes, whose structures are shown in FIGS. 2A and 2B.

TABLE 1

| Near Infrared Fluorochromes | | | | | |
|---|---|---|---|---|---|
| Fluoro-chrome | $\lambda$(nm) excitation | $\lambda$(nm) emission | Mol. Wt. | Extinct. Coef. | Quantum yield % |
| Cy5.5 | 675 | 694 | 1128.41 | 250,000 | 28.0 |
| Cy5 | 649 | 670 | 791.99 | 250,000 | 28.0 |
| IRD41 | 787 | 807 | 925.10 | 200,000 | 16.5 |
| IRD700 | 685 | 705 | 704.92 | 170,000 | 50.0 |
| NIR-1 | 663 | 685 | 567.08 | 75,000 | NA |
| LaJolla Blue | 680 | 700 | 5000.00 | 170,000 | 70.0 |

Intramolecular fluorescence quenching by non-activated probes can occur by any of various quenching mechanisms.

Several mechanisms are known, including resonance energy transfer between two fluorochromes. In this mechanism, the emission spectrum of a first fluorochrome should be very similar to the excitation of a second fluorochrome, which is in close proximity to the first fluorochrome. Efficiency of energy transfer is inversely proportional to $r^6$, where r is the distance between the quenched chromophore and excited chromophore. Self-quenching can also result from fluorochrome aggregation or excimer formation. This effect is strictly concentration dependent. Quenching also can result from a non-polar-to-polar environmental change.

To achieve intramolecular quenching, several strategies can be applied. They include: (1) linking a second fluorochrome, as an energy acceptor, at a suitable distance from the first fluorochrome; (2) linking fluorochromes to the backbone at high density, to induce self-quenching; and (3) linking polar fluorochromes in a vicinity of non-polar structural elements of the backbone and/or protective chains. Fluorescence is partially or fully recovered upon cleavage of the fluorochrome from neighboring fluorochromes and/or from a particular region, e.g., a non-polar region, of the probe.

The fluorochrome can be covalently linked to a fluorochrome attachment moiety, backbone, or spacer using any suitable reactive group on the fluorochrome and a compatible functional group on the fluorochrome attachment moiety, backbone, or spacer. For example, a carboxyl group (or activated ester) on a fluorochrome can be used to form an amide linkage with a primary amine such as the ε-amino group of the lysyl side chain on polylysine.

In some embodiments of the invention, the fluorochromes are linked directly to the backbone or linked to the backbone through nonbiodegradable spacers. In such embodiments, the fluorescence activation sites are in the backbone. Some probes of this type accumulate in tumor interstitium and inside tumor cells, e.g., by fluid phase endocytosis. By virtue of this preferential accumulation, such probes can be used to image tumor tissues, even if the enzyme(s) activating the probe are not tumor specific.

In preferred embodiments of the invention, fluorochromes are linked to the backbone through spacers containing fluorescence activation sites. Oligopeptide spacers can be designed to contain amino acid sequences recognized by specific proteases associated with target tissues.

Prostate Specific Antigen (PSA), is a 33 kD chymotrypsin-like serine protease is secreted exclusively by prostatic epithelial cells. Normally, this enzyme is primarily involved in post-ejaculation degradation of the major human seminal protein. Normally, serum concentrations of PSA are proportional to the volume of prostatic epithelium. The release of PSA from prostate tumor cells, however, is about 30-fold higher than that from normal prostate epithelium cells. Damages basal membrane and deranged tissue architecture allow PSA to be secreted directly into the extracellular space and into the blood. Although high levels of PSA can be detected in serum, the serum PSA exists as a complex with a1-antichymotrypsin protein, and is proteolytically inactive. Free, uncomplexed, activated PSA occurs in the extracellular fluid from malignant prostate tissues, and PSA activity can be used as a marker for prostate tumor tissue. prostate tumor tissue is highly enriched in PSA. Thus, spacers containing the amino acid sequence recognized by PSA can be used to produce a near infrared probe that undergoes fluorescence activation specifically in prostate tumor tissue. An example of a PSA-sensitive spacer is His-Ser-Ser-Lys-Leu-Gln-Gly (SEQ ID NO:2). Other PSA-sensitive spacers can be designed using information known in the art regarding the substrate specificity of PSA. See, e.g., 1997, Denmeade et al., *Cancer Res.* 57:4924–4930.

Cathepsin D is an abundant lysosomal aspartic protease distributed in various mammalian tissues. In most breast cancer tumors, cathepsin D is found at levels from 2-fold to 50-fold greater than levels found in fibroblasts or normal mammary gland cells. Thus, cathepsin D can be a useful marker for breast cancer. Spacers containing the amino acid sequence recognized by cathepsin D can be used to produce a near infrared probe that undergoes fluorescence activation specifically in breast cancer tissue. An example of a cathepsin D-sensitive spacer is the oligopeptide: Gly-Pro-Ile-Cys-Phe-Phe-Arg-Leu-Gly (SEQ ID NO:1). Other cathepsin D-sensitive spacers can be designed using information known in the art regarding the substrate specificity of cathepsin D. See, e.g., Gulnik et al., 1997, *FEBS Let.* 413:379–384.

When the fluorochromes are linked directly to the backbone, probe activation is by cleavage of the backbone. High fluorochrome loading of the backbone can interfere with backbone cleavage by activating enzymes such as trypsin. Therefore, a balance between fluorescence quenching and accessibility of the backbone by probe-activating enzymes. For any given backbone-fluorochrome combination (when activation sites are in the backbone) probes representing a range of fluorochrome loading densities can be produced and tested in vitro to determine the optimal fluorochrome loading percentage.

When the fluorochromes are linked to the backbone through activation site-containing spacers, accessibility of the backbone by probe-activating enzymes is unnecessary. Therefore, high loading of the backbone with spacers and fluorochromes does not significantly interfere with probe activation. In such a system, every lysine residue of polylysine can carry a spacer and fluorochrome, and every fluorochrome can be released by activating enzymes.

Preferential accumulation of a probe in a target tissue can be achieved or enhanced by binding a tissue-specific targeting moiety (targeting ligand) to the probe. The binding can be covalent or non-covalent. Examples of targeting moieties include a monoclonal antibody (or antigen-binding antibody fragment) directed against a target-specific marker, a receptor-binding polypeptide directed to a target-specific receptor, and a receptor-binding polysaccharide directed against a target-specific receptor. Antibodies or antibody fragments can be produced and conjugated to probes of this invention using conventional antibody technology (see, e.g., Folli et al., 1994, "Antibody-Indocyanin Conjugates for Immunophotodetection of Human Squamous Cell Carcinoma in Nude Mice," *Cancer Res.* 54:2643–2649; Neri et al., 1997, "Targeting By Affinity-Matured Recombinant Antibody Fragments of an Angiogenesis Associated Fibronectin Isoform," *Nature Biotechnology* 15:1271–1275). Similarly, receptor-binding polypeptides and receptor-binding polysaccharides can be produced and conjugated to probes of this invention using known techniques.

In Vitro Probe Testing

After a probe is designed and synthesized, it can be tested routinely in vitro to verify a requisite level of intramolecular fluorescence quenching before activation. Preferably, this is done by obtaining a fluorescence value for the intramolecularly quenched, fluorochrome-containing probe in a dilute, physiological buffer. This value is then compared to the fluorescence value obtained from an equimolar concentration of free fluorochrome in the same buffer, under the same fluorescence-measuring conditions. Preferably, this comparison will be done at a series of dilutions, to verify that the measurements are taking place on a linear portion of the fluorescence vs. fluorochrome concentration curve.

The molar amount of an intramolecularly-quenched fluorochrome on a probe can be determined by one of ordinary skill in the art using any suitable technique. For example, the molar amount can be determined readily by near infrared absorption measurements. Alternatively, it can be determined readily by measuring the loss of reactive linking groups on the backbone (or spacers), e.g., decrease in ninhydrin reactivity due to loss of amino groups.

After suitable intramolecular fluorescence quenching is verified, "de-quenching," i.e., fluorescence, upon exposure to an activating enzyme also can be verified in vitro. In preferred procedure, fluorescence of an intramolecularly-quenched probe is measured before and after treatment with an activating enzyme. If the probe has activation sites in the backbone (as opposed to in spacers), de-quenching should be tested at various levels of fluorochrome loading, where "loading" refers to the percentage of possible fluorochrome linkage sites on the backbone actually occupied by fluorochromes.

In addition, cells grown in culture can be used routinely to test intramolecularly-quenched near infrared fluorescence probes. Probe molecules free in cell culture medium should be non-detectable by fluorescence microscopy. Cellular uptake should result in probe activation and a fluorescence signal from probe-containing cells. Microscopy of cultured cells thus can be used to verify that activation takes place upon cellular uptake of a probe being tested. Microscopy of cells in culture is also a convenient means for determining whether activation occurs in one or more subcellular compartments.

In Vivo Optical Imaging

Although the invention involves novel fluorescence probes, general principles of fluorescence, optical image acquisition, and image processing can be applied in the practice of the invention. For a review of optical imaging techniques, see, e.g., Alfano et al., 1997, "Advances in Optical Imaging of Biomedical Media," *Ann. NY Acad. Sci* 820:248–270.

An imaging system useful in the practice of this invention can include three basic components. The first is a source of nearly monochromatic, near infrared light. This can be provided by filtered white light. For example, light from a 150-watt halogen lamp can be passed through a suitable bandpass filter commercially available from Omega Optical (Brattleboro, Vt.). The second basic component is a high pass filter (700 nm), which separates the fluorescence emissions from the excitation light. A suitable high pass filter also can be purchased from Omega Optical. The third basic component is a low-light (cooled) CCD camera with appropriate macro lens attachments. Selecting suitable components and assembling them into a suitable optical imaging system is within ordinary skill in the art.

In order that the invention may be more fully understood, the following examples are provided. It should be understood that these examples are for illustrative purposes only and are not to be construed as limiting the invention in any way.

EXAMPLES

Synthesis of Near Infrared Fluorescence Probes

We synthesized three different intramolecularly-quenched near infrared fluorescence probes by conjugating a commercially-available fluorochrome known as Cy5.5 (absorption=675 nm, emission=694 nm; Amersham, Arlington Heights, Ill.) to PL-MPEG (average molecular weight approx. 450 kD). The three probes differed in attachment of the fluorochrome to the polylysine backbone. In a probe designated "Cy-PL-MPEG," the Cy5.5 was linked directly to the $\epsilon$-amino group of the polylysine side chains at various densities, which ranged from 0.1% to 70% derivatization of the $\epsilon$-amino groups. In a probe designated, "Cy-RRG-PL-MPEG," the Cy5.5 fluorochrome was linked to the polylysine by a a spacer consisting of Arg-Arg-Gly. In a probe designated "Cy-GPICFFRLG-PL-MPEG," the Cy 5.5 fluorochrome was linked to the polylysine by a a spacer consisting of Gly-Pro-Ile-Cys-Phe-Phe-Arg-Leu-Gly (SEQ ID NO:1). Trypsin and trypsine-like proteases are capable of cleaving the polylysine backbone of Cy-PL-MPEG, when it is only partially derivatized.

Probes Cy-RRG-PL-MPEG and Cy-GPICFFRLG-PL-MPEG were designed to allow fluorochrome cleavage of the spacer, but not necessarily the backbone. For example the peptide spacer RRG, sensitive to trypsin cleavage, was used to derivatize the PL-MPEG, and then Cy5.5 was linked to the N-terminus of the RRG spacers. The cathepsin D sensitive peptide spacer, GPICFFRLG (SEQ ID NO:1), was similarly used to derivatize the PL-MPEG.

Cy5.5, commercially available as a monofunctional NHS-ester (Amersham, Arlington Heights, Ill.), was used according to the vendor's instructions, to label free $\epsilon$-amino groups of the polylysine backbone in PL-MPEG. Cy5.5 was added to a pre-mixed MPEG-PL solution (0.2 mg PL-MPEG in 1 ml 80 mM sodium bicarbonate solution) to a final concentration of 17 $\mu$M. After three hours, the reaction mixture was applied to a Sephadex™ G-25 (Pharmacia) column (12 cm) for separation of the reaction product (Cy-PL-MPEG) from the unreacted fluorochrome and other low-molecular weight components of the reaction mixture. Average fluorochrome loading was about 20%, i.e., 11 out of 55 free amino groups on the PL-MPEG labeled with Cy5.5 (based on TNBS assay and absorption measurement).

Figure 3A:
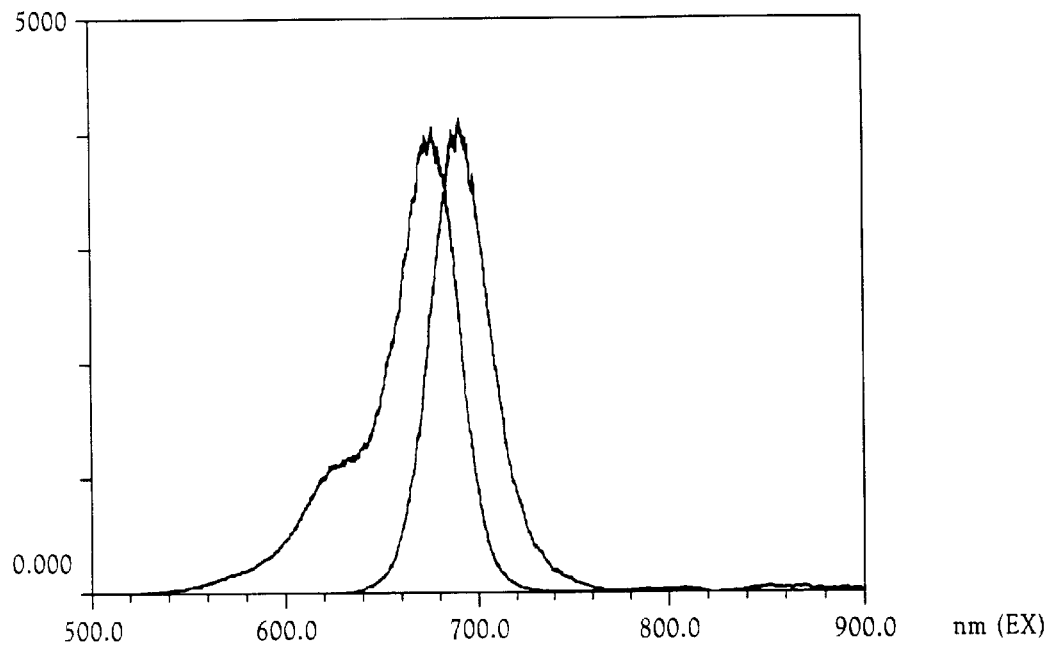
FIGS. 3A and 3B are spectrophotometer scans of the near infrared fluorochrome, Cy5.5, before (FIG. 3A) and after (FIG. 3B) covalent linkage to PL-MPEG.
Figure 3B:
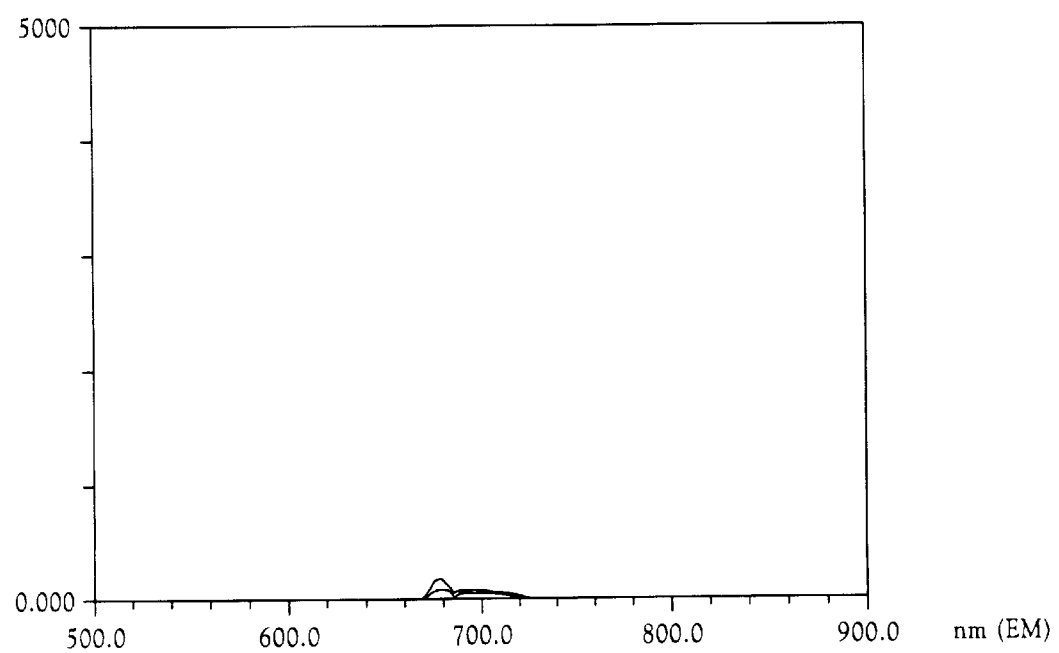

FIG. 3A shows the excitation and emission spectra of Cy5.5 free in solution. FIG. 3B shows the excitation and emission spectra of Cy5.5 fluorochromes of Cy-PL-MPEG. The excitation and emission wavelengths of Cy5.5 are 648 nm and 694 nm, respectively. There was a marked difference in the level of fluorescence of the free Cy5.5 and the Cy-PL-MPEG. The fluorescence level of the Cy-MPEG-PL was approximately 30-fold lower than that of the unbound Cy5.5.

Figure 4:
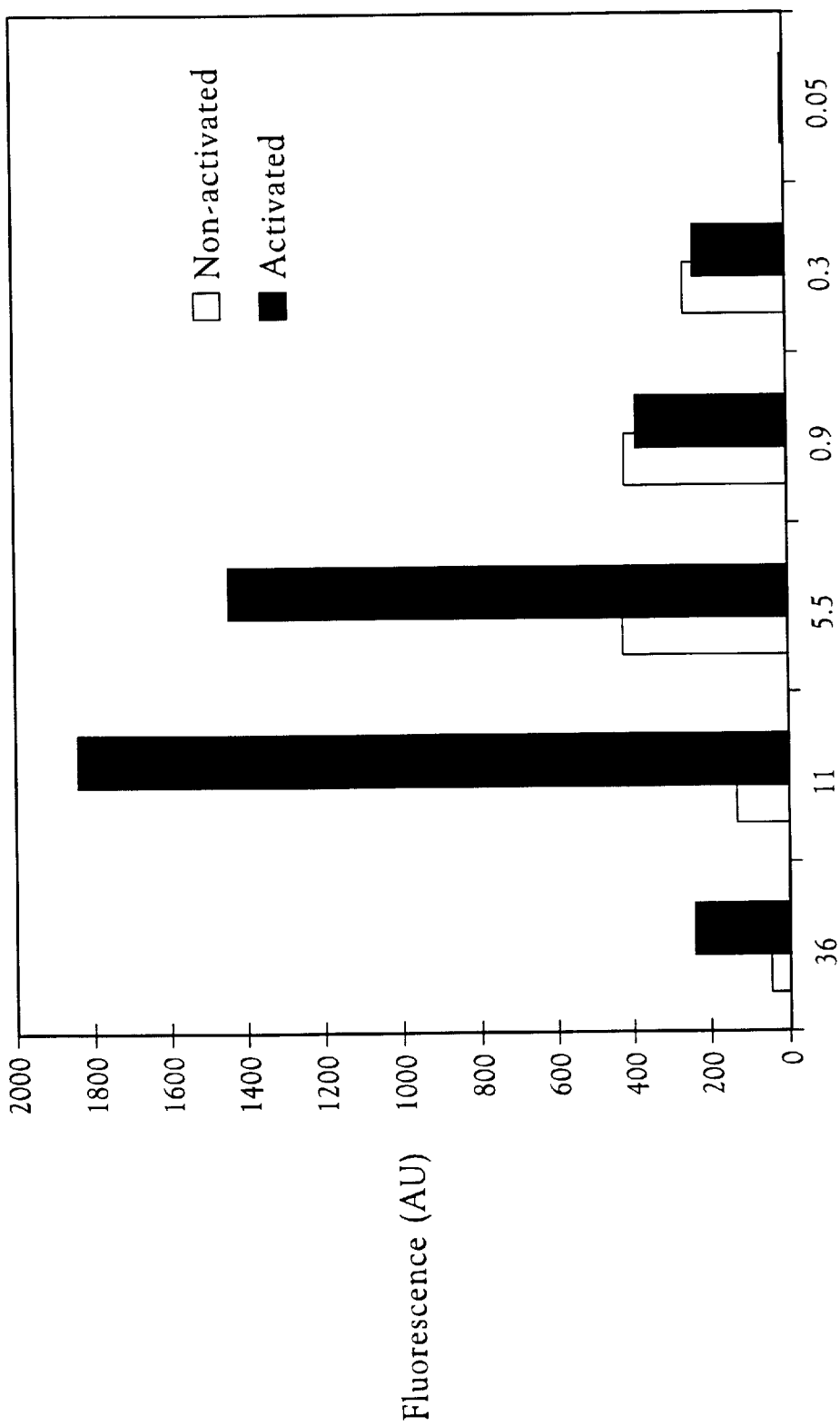
FIG. 4 is a bar graph summarizing data on intramolecular quenching and probe activation. The data were obtained using Cy-PL-MPEG probes with different levels of fluorochrome loading.

In subsequent studies, we determined the effect of fluorochrome loading (i.e., percentage of $\epsilon$-amino groups on the polylysine backbone occupied by fluorochrome) on the optical properties of the probe. FIG. 4 shows the relative fluorescent signal of Cy(n)-MPEG-PL (white bars) as a function of percentage of $\epsilon$-amino groups on the polylysine backbone occupied by fluorochrome. At 20% loading (11 of 55 groups) and higher, intramolecular quenching was observed, and the fluorescence signal was lowered in comparison to probes with lower fluorochrome loading. After trypsin cleavage of the backbone, fluorescence signal was recovered, as shown by the black bars in FIG. 4. Maximum fluorescence recovery was obtained at 20% loading (15-fold fluorescence signal increase upon activation). Recovery was reduced when at loading greater than 20%. This may have been due to steric hinderance and the need for free lysine groups for efficient cleavage of the backbone.

Probe Activation in Cell Culture

The next step in testing the functional imaging probe was to perform cell culture experiments. We expected that non-internalized Cy-PL-MPEG would be non-detectable by fluorescence microscopy, and that cellular uptake would lead to activation of the probe, with a resulting fluorescence signal. Data obtained using amelanotic B16 melanoma cells confirmed our prediction and showed that: (1) the non-activated probe is non-fluorescent, (2) the probe is taken up by this cell line, and (3) cellular uptake results in activation of the probe and fluorescence signal detection.

In this experiment we compared a bright field image outlining B16 cells to: (1) the same field under near infrared fluorescence conditions when Cy-MPEG-PL was added to the cells, near time-zero; and (2) after allowing time for intracellular uptake of the probe (data not shown). The cells were not detectable by near infrared fluorescence near time-zero, but the cells were clearly visible (due to intracellular fluorescence) after cellular uptake of the probe, i.e., at about two hours. This experiment demonstrated that our imaging probe detectably changed its optical properties in a target cell-dependent manner.

In Vivo Imaging

In vivo mouse imaging was carried out using a system composed of three main parts: light source, platform/holder, and image recording device. A fiber optic light bundle with a 150 W halogen bulb (Fiberlite high intensity illuminator series 180, Dolan-Jennen Industries) provided broad spectrum white light. A sharp cut off band pass optical filter (Omega Filter Corp., Brattleboro, Vt.) was mounted at the end of the fiber optic bundle to create a uniform excitation source in the 610–650 nm range. The light was placed approximately 15 cm above the imaging platform to provide homogenous illumination of the entire mouse. The platform itself was a matte black surface that decreased the number of excitation photons reflected (and possibly detected) by the recording device.

Fluorescent (emission) photons were selected using a low pass filter with a sharp cut off at 700 nm (Omega Filter Corp.). Cy5.5 dye has an excitation peak at approximately 670 nm, with a broad shoulder extending below 610 nm. Peak emission is at 694 nm. Sharp cut-off filters with more than 5 OD attenuation combined with widely spaced frequencies for the filter set markedly decreased "cross talk" of incident excitation photons recorded as fluorescent emission signal. The narrow angle between light source and recording device ensured that only fluorescent emission photons or scattered photons that interacted with the mouse tissue reached the low pass filter.

For image recording, the low-pass filter was mounted on a low power microscope (Leica StereoZoom 6 photo, Leica microscope systems, Heerbrugg, Switzerland). A low light CCD (SenSys 1400, 12 bit cooled CCD, Photometrics, Tuscon, Ariz.) recorded the fluorescent emission images. Images were transferred to a PowerMac 7600/120 PC (Apple Computer, Cupertino, Calif.) and processed using IPLab Spectrum 3.1 software (Signal Analytics Corp., Vienna, Va.). Post processing included standard routines to exclude bad CCD pixels, and superimposition routines to overlay emission images with localization images of the entire mouse obtained using a second white light source. Typical acquisition time was 30 seconds for the near infrared emission images, and 1 second for the white light (non-selective images).

We tested the near intramolecularly-quenched infrared fluorescence probe ($Cy_{11}$-PL-MPEG; 20% fluorochrome loading) in tumor-bearing mice. Nude mice bearing tumor line 9L or LX1 received 2 nmol of $Cy_{11}$-PL-MPEG intravenously. The mice were imaged by near infrared light immediately, and up to 36 hours after intravenous administration of the probe. An increase in fluorescence signal within tumor was observed as a function of time, as the probe was internalized into tumor cells and became activated by endosomal hydrolases.

Figure 5A:
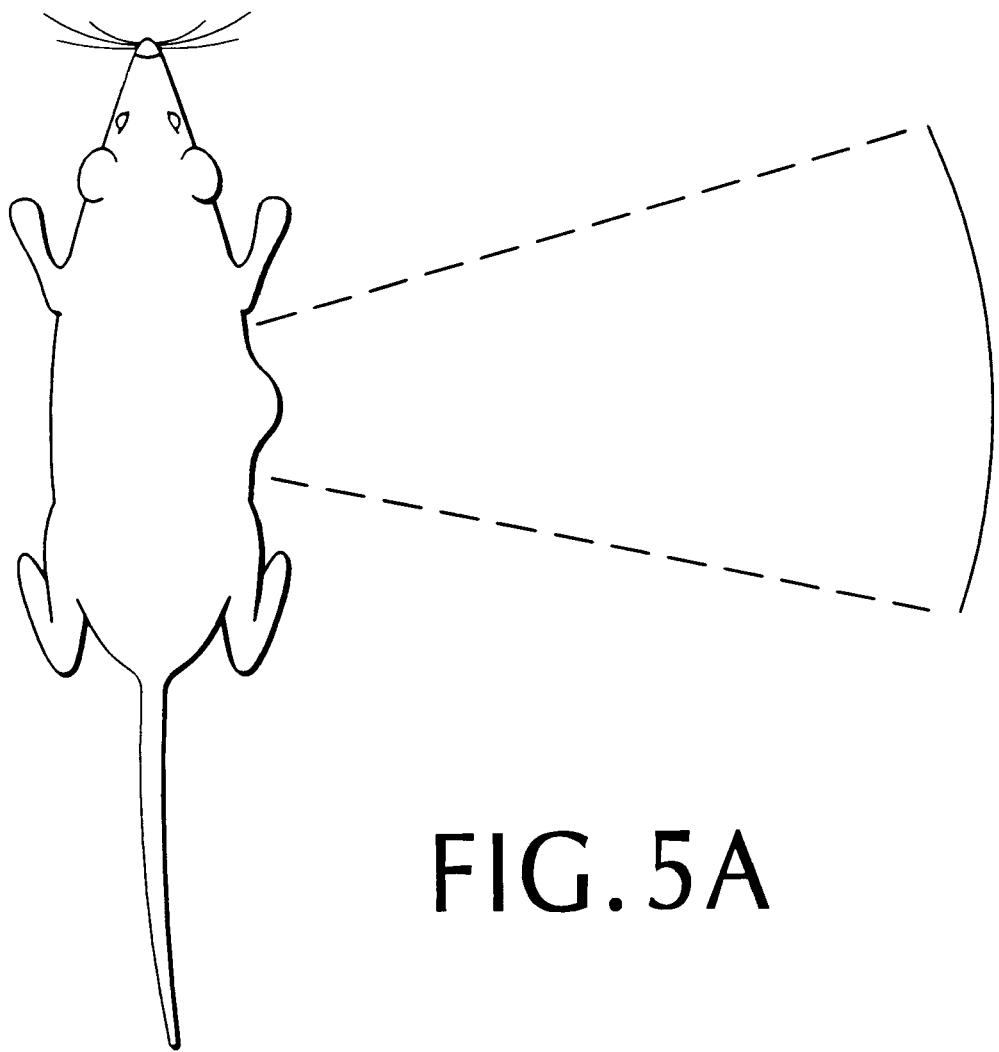
FIG. 5A is a schematic diagram illustrating the location of the murine flank tumor shown in FIGS. 5B and 5C.
Figure 5B:
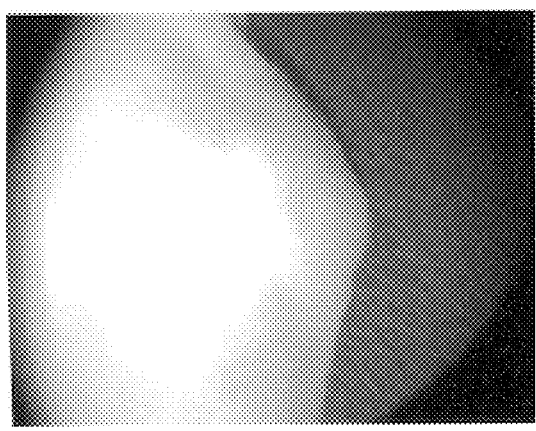
FIG. 5B is a visible light photograph of the skin covering a human flank tumor in a 9L-bearing nude mouse.
Figure 5C:
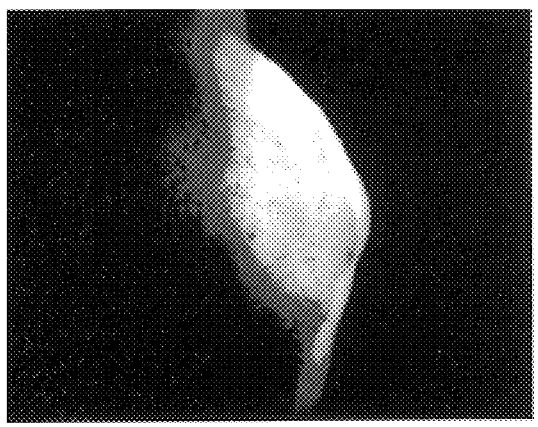
FIG. 5C is a near infrared fluorescence image of the tumor in FIG. 5B.

FIG. 5A is a schematic diagram of the imaged mouse, illustrating the location of tumor shown in FIGS. 5B and 5C. FIG. 5B is visible light photograph of the skin covering a tumor on the side of a nude mouse into which the $Cy_{11}$-PL-MPEG probe was injected. FIG. 5C is a corresponding near infrared fluorescence image. The tumor is visible as an area of intense fluorescence, in contrast to the surrounding tissue.

Other embodiments are within the following claims.

We claim:

1. An intramolecularly-quenched fluorescence probe comprising a polymeric backbone and a plurality of near infrared fluorochromes covalently linked to the backbone at fluorescence-quenching interaction-permissive positions separable by enzymatic cleavage at fluorescence activation sites.

2. The probe of claim 1, wherein the backbone is a polypeptide.

3. The probe of claim 2, wherein the polypeptide is polylysine.

4. The probe of claim 1, further comprising a plurality of protective chains covalently linked to the backbone.

5. The probe of claim 4, wherein the protective chains are selected from the group consisting of polyethylene glycol, methoxypolyethylene glycol, methoxypolypropylene glycol, copolymers of polyethylene glycol and methoxypolypropylene glycol, dextran, and polylactic-polyglycolic acid.

6. The probe of claim 4, wherein the backbone is polylysine and the protective chains are methoxypolyethylene glycol.

7. The probe of claim 1, wherein the fluorescence activation sites are located in the backbone.

8. The probe of claim 7, wherein the fluorochromes are linked to $\epsilon$-amino groups of polylysine.

9. The probe of claim 1, wherein each fluorochrome is linked to the backbone by a spacer containing a fluorescence activation site.

10. The probe of claim 9, wherein the spacers are oligopeptides.

11. The probe of claim 10, wherein the oligopeptide is selected from the group consisting of Arg-Arg;

Arg-Arg-Gly;

Gly-Pro-Ile-Cys-Phe-Phe-Arg-Leu-Gly (SEQ ID NO:1); and

His-Ser-Ser-Lys-Leu-Gln-Gly (SEQ ID NO:2).

12. The probe of claim 1, wherein the fluorochromes are selected from the group consisting of Cy5.5, Cy5, IRD41, IRD700, NIR-1, and LaJolla Blue.

13. The probe of claim 1, wherein the fluorochromes are covalently linked to amino groups on the backbone or spacers by means of amide bonds.

14. The probe of claim 1, further comprising a targeting moiety.

15. The probe of claim 14, wherein the targeting moiety is selected from the group consisting of: an antibody, an antibody fragment, a receptor-binding polypeptide, and a receptor-binding polysaccharide.

16. An in vivo optical imaging method comprising:

(a) administering to a living animal or human an intramolecularly-quenched fluorescence probe that accumulates in a target tissue, and comprises a fluorochrome attachment moiety and a plurality of near infrared fluorochromes covalently linked to the fluorochrome attachment moiety at fluorescence-quenching interaction-permissive positions separable by enzymatic cleavage at fluorescence activation sites;

(b) allowing time for (1) the probe to accumulate in the target tissue, and (2) enzymes in the target tissue to activate the probe by enzymatic cleavage at a fluorescence activation site, if the target tissue is present;

(c) illuminating the target tissue with near infrared light of a wavelength absorbable by the fluorochromes;

(d) detecting fluorescence emitted by the fluorochromes, and forming an optical image of the target tissue, if present.

17. The method of claim 16, wherein the fluorochrome attachment moiety is a polymeric backbone.

18. An in vivo optical imaging method comprising:

(a) administering to a living animal or human an intramolecularly-quenched fluorescence probe comprising a fluorochrome attachment moiety and a plurality of near infrared fluorochromes covalently linked to the fluorochrome attachment moiety at fluorescence-quenching interaction-permissive positions separable by enzymatic cleavage at fluorescence activation sites, which enzymatic cleavage occurs in a target tissue;

(b) allowing time for enzymes in the target tissue to activate the probe by enzymatic cleavage at a fluorescence activation site, if the target tissue is present;

(c) illuminating the target tissue with near infrared light of a wavelength absorbable by the fluorochromes;

(d) detecting fluorescence emitted by the fluorochromes, and forming an optical image of the target tissue, if present.

19. The method of claim 18, wherein the fluorochrome attachment moiety is a polymeric backbone.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (xi) SEQUENCE DESCRIPTION: SEQ ID NO:1:

Gly Pro Ile Cys Phe Phe Arg Leu Gly
1               5

(2) INFORMATION FOR SEQ ID NO:2:

(i) SEQUENCE CHARACTERISTICS:
      (A) LENGTH: 7 amino acids
      (B) TYPE: amino acid
      (D) TOPOLOGY: linear

```
        (ii) MOLECULE TYPE: peptide (xi) SEQUENCE DESCRIPTION: SEQ ID NO:2:

His Ser Ser Lys Leu Gln Gly
 1               5
```